United States Patent [19]
Wanzke et al.

[11] Patent Number: 5,157,172
[45] Date of Patent: Oct. 20, 1992

[54] PROCESS FOR THE PREPARATION OF 1,1,1-TRIFLUORO-2-CHLOROETHANE

[75] Inventors: Wolfgang Wanzke, Frankfurt am Main; Günter Siegemund, Hofheim am Taunus; Thomas Müller, Bad Homburg, all of Fed. Rep. of Germany

[73] Assignee: Hoechst Aktiengesellschaft, Frankfurt am Main, Fed. Rep. of Germany

[21] Appl. No.: 844,948

[22] Filed: Mar. 2, 1992

Related U.S. Application Data

[63] Continuation of Ser. No. 552,259, Jul. 12, 1990, abandoned.

[30] Foreign Application Priority Data

Jul. 14, 1989 [DE] Fed. Rep. of Germany ....... 3923256

[51] Int. Cl.$^5$ ............................................ C07C 17/08
[52] U.S. Cl. ..................................................... 570/168
[58] Field of Search ........................................ 570/168

[56] References Cited

U.S. PATENT DOCUMENTS 2,885,427  5/1959  Ruh et al. .
3,755,477  8/1973  Firth et al. .
4,547,483  10/1985  Muller et al. .

FOREIGN PATENT DOCUMENTS 1246703  2/1962  Fed. Rep. of Germany .

*Primary Examiner*—Alan Siegel

[57] ABSTRACT

The invention relates to a process for the preparation of 1,1,1-trifluoro-2-chloroethane from trichloroethene and hydrogen fluoride in the gas phase. In this process a catalyst containing chromium and magnesium is used, which catalyst is obtainable by precipitating chromium-(III) hydroxide by reacting 1 mole of a water-soluble chromium(III) salt with at least 1.5 mol of magnesium hydroxide or magnesium oxide in the presence of water, converting the reaction mixture into a paste containing chromium hydroxide and a magnesium salt and then drying the paste and treating it at temperatures of 20° to 500° C. with hydrogen fluoride.

8 Claims, No Drawings

PROCESS FOR THE PREPARATION OF 1,1,1-TRIFLUORO-2-CHLOROETHANE

This application is a continuation of application Ser. No. 07/552,259 filed on Jul. 12, 1990 now abandoned.

DESCRIPTION

The invention relates to a process for the preparation of 1,1,1-trifluoro-2-chloroethane by reaction of trichloroethene with hydrogen fluoride in the gas phase.

1,1,1-Trifluoro-2-chloroethene (which hereinafter is also designated as trifluorochloroethane) can be used as a versatile intermediate for the preparation of other trifluoromethyl compounds. 1,1,1,2-Tetrafluoroethane (R 134a), which is a suitable chlorine-free substitute for difluorodichloromethane (R 12) in refrigeration and air-conditioning technology, is obtained, for example, by further chlorine-fluorine exchange. In addition, trifluoroethanol, trifluoroacetyl chloride and the inhalation anesthetic trifluorochlorobromoethane can also be prepared from trifluorochloroethane.

It is already known that trifluorochloroethane can be obtained in the reaction of trichloroethene with hydrogen fluoride over suitable catalysts not only in the gas phase but also in the liquid phase.

Catalysts which have been described for the gas phase reaction are predominantly solids which are composed either completely of chromium(III) compounds or contain a chromium(III) salt on a support material such as alumina.

However, the results obtained in the previously known preparation processes are unsatisfactory in several respects:

1. The trichloroethene used is only converted incompletely.
2. Apart from trifluorochloroethane, various by-products are additionally formed (lack of selectivity).
3. The catalysts rapidly lose activity.

British Patent 1,025,759 describes the reaction of trichloroethene with hydrogen fluoride over chromyl fluoride catalysts, which are prepared from hydrated chromium(III) oxide or chromium(III) hydroxide precipitated under basic conditions. By means of these catalysts, the hitherto highest conversions have been achieved (86–96%). The yields of trifluorochloroethane, relative to converted trichloroethene, were 82–92%.

U.S. Pat. No. 3,755,477 mentions a trifluorochloroethane yield of 85% for a chromyl fluoride catalyst prepared from chromium(III) hydroxide and additionally activated with water vapor.

Investigations of the chromyl fluoride catalysts described have shown that the conversion of trichloroethene drops considerably after a continuous exposure for 50–100 hours, so that these catalysts are not suitable for the industrial preparation of trifluorochloroethane.

The processes described in U.S. Pat. No. 2,885,427 and German Patent 1,246,703, which use other chromium-containing catalysts, give even more unfavorable yields of trifluorochloroethane.

It has now been found that the catalyst described in EP-OS 130,532=U.S. Pat. No. 4,547,483, which is composed of magnesium fluoride and a fluorine-containing chromium(III) compound, makes it possible to convert trichloroethene into trifluorochloroethane with surprising selectivity and almost quantitative conversion.

The invention relates to a process for the preparation of 1,1,1-trifluoro-2-chloroethane from trichloroethene and hydrogen fluoride in the gas phase, which comprises using a catalyst containing chromium and magnesium, which catalyst is obtainable by precipitating chromium(III) hydroxide by reacting 1 mole of a water-soluble chromium(III) salt with at least 1.5 mol of magnesium hydroxide or magnesium oxide in the presence of water, converting the reaction mixture into a paste containing chromium hydroxide and a magnesium salt and then drying the paste and treating it at temperatures of 20° to 500° C. with hydrogen fluoride.

The gas phase reaction according to the invention is particularly efficient under elevated pressure, since the high conversion is then maintained over a particularly long period. During the reaction, a pressure of 1–26 bar, preferably 2–17 bar, particularly preferably 4–10 bar, is adjusted in the reactor by means of a control valve.

If the activity diminishes, the catalyst can be rapidly regenerated by passing air at elevated temperatures over it, as a result of which it then again reaches its original performance. This regeneration process can be repeated several times without damaging the catalyst. A pretreatment (conditioning) with air at temperatures of 100° to 500° C. has the effect that the catalyst reaches its maximum activity right at the start of the reaction.

The process according to the invention can be carried out, for example, in such a manner that the starting materials trichloroethene and hydrogen fluoride are continuously fed to an evaporator made of stainless steel or nickel. The temperature of the evaporator is not critical but must be sufficient to convert both components at the chosen pressure completely into the gas phase. The gaseous starting materials enter, if appropriate via a preheating zone and a gas mixer, the reactor which contains a bed of the catalyst described in EP-OS 130,532. The reactor is likewise made of stainless steel or nickel and can be used in various technical designs, for example as shaft, tubular or annular reactor.

The temperature of the catalyst bed is maintained at 150°–450° C., preferably at 250°–350° C., by heating the reactor.

To achieve complete conversion of the trichloroethene, the hydrogen fluoride is preferably used in excess. The molar ratio of hydrogen fluoride/trichloroethene is in general at least 3:1; the upper limit of the molar ratio only depends on economical considerations. Preferably it is 4:1 to 8:1, in particular 4:1 to 6:1.

The process according to the invention is illustrated in more detail by the examples which follow.

TEST REPORT

A (Preparation of the Catalyst According to EP-OS 130,532)

200 g of $Cr(NO_3)_3 \times 9\ H_2O$ were dissolved in 1 l of water. This solution was added to a mixture of 500 g of magnesium oxide and 240 g of graphite, and the resulting paste-like material was intimately kneaded.

The paste-like reaction product was then granulated to give cube-shaped pieces (length of edge 0.5 cm) and dried at 100° C. for 16 hours.

1 l (pump volume) of the dried catalyst pieces (=600 g) were treated in a stainless steel or nickel tube of 5 cm clearance and 100 cm length at 200° C. with 15 mol of hydrogen fluoride. The duration of the hydrogen fluoride treatment was about 6 hours. For this treatment, the HF was diluted with $N_2$. The fluorination catalyst obtained had a chromium content of 2.3% by weight.

B (Preparation of the Catalyst According to EP-OS 130,532)

200 g of $Cr(NO_3)_3 \times 9 H_2O$ were dissolved in 278 ml of water. This solution was added to a mixture of 138 g of magnesium oxide and 136 g of graphite. The further processing and hydrogen fluoride treatment was carried out in accordance with test report A. The ready-to-use fluorination catalyst contained 4.3% by weight of chromium.

EXAMPLE 1

56 g of trichloroethene and 43 g of hydrogen fluoride per hour were passed as a gas over 1 l of the catalyst prepared by the method of test report A in a tubular reactor which was maintained at a temperature of 300° C. by means of an electric heating coil.

The tubular reactor was the same which had already been used for the hydrogen fluoride treatment in the preparation of the catalyst.

The gaseous reaction products leaving the reactor were fed to a wash tank filled with water or potassium hydroxide solution, in which the hydrogen chloride formed and excess hydrogen fluoride were absorbed.

The gaseous water-insoluble reaction products were analyzed by gas chromatography.

After 24 hours at atmospheric pressure, the conversion was 98.6%, relative to the trichloroethene used. The selectivity for trifluorochloroethane was 98.7%, relative to converted trichloroethene.

The reaction product contained 97.3% by weight of $CF_3CH_2Cl$.

After 170 hours at atmospheric pressure, the conversion was 95.0% and the selectivity 96.3%.

EXAMPLE 2

The catalyst prepared by the method of test report A was used for the reaction of trichloroethene with hydrogen fluoride in the same experimental set-up as in Example 1. 120 g of trichloroethene per hour and 92 g of hydrogen fluoride per hour were passed as a gas over the catalyst at 300° C.

After 24 hours at a superatmospheric pressure of 9 bar, the conversion was 99.8%, relative to the trichloroethene used. Selectivity for trifluorochloroethane was 97.7%, relative to converted trichloroethene.

The reaction product contained 97.5% by weight of $CF_3CH_2Cl$.

After 160 hours at 10 bar, the conversion was 99.3% and the selectivity 97.4%.

EXAMPLE 3

The catalyst prepared by the method of test report A was used in the same experimental set-up as in Example 1. 120 g of trichloroethene per hour and 82 g of hydrogen fluoride per hour were passed as a gas over the catalyst, which corresponds to a molar ratio of $HF/C_2HCl_3$ of 4.5:1. The reaction temperature was 300° C. After 20 hours at a pressure of 10 bar, the conversion was found to be 95.5%, relative to the trichloroethene used, and the selectivity for trifluorochloroethane was found to be 95.6%, relative to the trichloroethene used.

The reaction product contained 91.3% by weight of $CF_3CH_2Cl$.

EXAMPLE 4

1 liter of a catalyst prepared by the method of test report A showed the following result in the same experimental set-up as in Example 1 after 420 hours of continuous reaction of trichloroethene with hydrogen fluoride at alternating test conditions in a subsequent test (300° C., 10 bar, 120 g/h of trichloroethene, 92 g/h of hydrogen fluoride):
Conversion: 91.6%
Selectivity: 93.1%

To regenerate the catalyst, 400 l of air per hour were passed over the catalyst at 300° C. (duration: 20 hours).

Trichloroethene and hydrogen fluoride were then reacted under the same conditions as in the test by passing them over the catalyst.

After 24 hours, the following result was found by gas chromatography:
Conversion: 99.8%
Selectivity: 97.7%

EXAMPLE 5

The catalyst prepared by the method of test report B was used in the same experimental set-up as in Example 1. 56 g of trichloroethene per hour and 43 g of hydrogen fluoride per hour were passed as a gas over the catalyst at 300° C.

After 5 hours at atmospheric pressure, the conversion was 98.5%, relative to the trichloroethene used. The selectivity for trifluorochloroethane was 97.6%, relative to converted trichloroethene.

The reaction product contained 96.1% by weight of $CF_3CH_2Cl$.

EXAMPLE 6

The catalyst prepared by the method of test report A was used in the same experimental set-up as in Example 1. 105 g of trichloroethene per hour and 80 g of hydrogen fluoride per hour were passed as a gas over the catalyst. The reaction temperature was 400° C.

Within 20 hours, 1870 g of a product having a $CF_3CH_2Cl$ content of 50.6% by weight were obtained.

EXAMPLE 7

The catalyst prepared by the method of test report A was used in the same experimental set-up as in Example 1. 130 g of trichloroethene per hour and 100 g of hydrogen fluoride per hour were passed as a gas over the catalyst.

The reaction temperature was 250° C.

Within 20 hours, 2285 g of a product having a $CF_3CH_2Cl$ content of 88.3% by weight were obtained.

We claim:

1. A process for the preparation of 1,1,1-trifluoro-2-chloroethane from trichloroethene and hydrogen fluoride in the gas phase, which comprises using a catalyst containing chromium and magnesium, which catalyst is obtainable by precipitating chromium(III) hydroxide by reacting 1 mole of a water-soluble chromium(III) salt with at least 1.5 mol of magnesium hydroxide or magnesium oxide in the presence of water, converting the reaction mixture into a paste containing chromium hydroxide and a magnesium salt and then drying the paste and treating it at temperatures of 20° to 500° C. with hydrogen fluoride.

2. The process as claimed in claim 1, wherein the reaction of trichloroethene with hydrogen fluoride is carried out in the temperature range of 150°–450° C.

3. The process as claimed in claim 1, wherein the reaction of trichloroethene with hydrogen fluoride is carried out in the temperature range of 250°–350° C.

4. The process as claimed in claim 1, wherein the reaction of trichloroethene with hydrogen fluoride is carried out under a pressure of 1–25 bar.

5. The process as claimed in claim 1, wherein the reaction of trichloroethene with hydrogen fluoride is carried out under a pressure of 2–17 bar.

6. The process as claimed in claim 1, wherein the reaction of trichloroethene with hydrogen fluoride is carried out under a pressure of 4–10 bar.

7. The process as claimed in claim 1, wherein hydrogen fluoride and trichloroethene are used in a molar ratio of 4:1 to 8:1.

8. The process as claimed in claim 1, wherein the catalyst is conditioned before the reaction at temperatures of 100°–500° C. with air and is regenerated in the same manner upon losing activity.

* * * * *